United States Patent [19]

Schaefer et al.

[11] Patent Number: 4,897,861
[45] Date of Patent: Jan. 30, 1990

[54] PRIMARY RADIATION DIAPHRAGM FOR X-RAY DIAGNOSTICS EQUIPMENTS

[75] Inventors: Willi Schaefer; Guenter Bartmann, both of Erlangen; Michael Meyer, Eckersdorf, all of Fed. Rep. of Germany

[73] Assignee: Siemens Aktiengesellschaft, Berlin and Munich, Fed. Rep. of Germany

[21] Appl. No.: 208,987

[22] Filed: Jun. 20, 1988

[30] Foreign Application Priority Data

Aug. 26, 1987 [DE] Fed. Rep. of Germany ....... 8711572

[51] Int. Cl.⁴ ................................................. G21K 1/04
[52] U.S. Cl. ..................................... 378/150; 378/152
[58] Field of Search ............... 378/152, 159, 147, 153, 378/149, 150, 151, 157, 160

[56] References Cited

U.S. PATENT DOCUMENTS

| | | |
|---|---|---|
| 3,631,249 | 12/1971 | Freide et al. . |
| 3,829,701 | 8/1974 | Hura . |
| 3,980,407 | 9/1976 | Hill ........................................ 378/152 |
| 4,472,828 | 9/1984 | Ferlie . |
| 4,514,859 | 4/1985 | Holzermer ........................... 378/152 |
| 4,672,652 | 6/1987 | Huettenrauch . |
| 4,752,947 | 6/1988 | Telorack ............................... 378/152 |
| 4,754,147 | 6/1988 | Maughan et al. .................... 378/152 |

FOREIGN PATENT DOCUMENTS

| | | |
|---|---|---|
| 0184695 | 6/1986 | European Pat. Off. . |
| 2053089 | 5/1972 | Fed. Rep. of Germany ...... 378/153 |
| 0197773 | 4/1978 | U.S.S.R. ............................... 378/153 |

Primary Examiner—Craig E. Church
Attorney, Agent, or Firm—Hill, Van Santen, Steadman & Simpson

[57] ABSTRACT

The diaphragm plates are individually adjustable in two-dimensional fashion. Semi-transparent diaphragm sections at the edges of the diaphragm plates limiting the radiation are adjustable perpendicular to the respective edge with a lever linkage such that the semi-transparent region becomes larger when the diaphragm is closed. A feedback control unit is present for operation. This feedback control unit has two operating pieces as an operating mechanism, which are displaceable by a user to positions similar to the diaphragm plates, and are electrically coupled to the feedback control unit to cause movement of the diaphragm plates to a position corresponding to the position of the operating plates.

4 Claims, 4 Drawing Sheets

PRIMARY RADIATION DIAPHRAGM FOR X-RAY DIAGNOSTICS EQUIPMENTS

BACKGROUND OF THE INVENTION

1. Field of the Invention

The present invention is directed to primary radiation diaphragms for x-ray diagnostics equipment, and in particular to such radiation diaphragms wherein the diaphragm plates are adjustably seated limiting a slot, and including a means for controlling the adjustment motion of the diaphragm plates.

2. Description of the Prior Art

A primary radiation diaphragm having a mechanism for controlling the adjustment motion of the diaphragm plates to selectively position a slot defined by the plates is known. This primary radiation diaphragm includes two diaphragm plates adjustable perpendicular to the longitudinal direction of the diaphragm slot. The slot in the known diaphragm has the same width at every location in every diaphragm position. A problem arises in practice when organs and body parts are to be gated, wherein the optimum shape of the gated field deviates from a rectangular shape.

SUMMARY OF THE INVENTION

It is the object of the present invention to fashion a primary radiation diaphragm limiting a slot and controlling the adjustment motion of the diaphragm plates such that the shape of the gated field is optimally adaptable to the respective requirements.

The above object is achieved in accordance with the principles of the present invention in a primary radiation diaphragm wherein the diaphragm plates are individually adjustable in a two-dimensional fashion. This adjustability makes it posible to centrally and eccentrically adjust the slot. The adjustability also allows selection of a V-shaped slot form. Thus, an optimum adaptation of the gated field to, for example, specific bone regions is possible.

An embodiment of the invention has semi-transparent (i.e., semi-transparent to x-radiation) diaphragm sections respectively carried at the edges of the diaphragm plates limiting the radiation which are adjustable with a lever linkage perpendicular to the respective edge such that the semitransparent region is set dependent on the diaphragm aperature. In the known primary radiation diaphragm, a semi-transparent region is provided at the diaphragm edges that is still penetrated by x-radiation but which noticeably attenuates the x-ratiation. Instruments that, for example, are introduced into an operating field are still visible in the semi-transparent region, so that it is easier for the technician to position the instruments. Conversely, regions of the patient that are unimportatnt for diagnostics are not unnecessarily penetrated by x-radiation. In the improvement of the invention, the semi-transparent region is not rigidly prescribed but is automatically set dependent on the diaphragm aperature. Given a small slot, the semi-transparent region must be largerthan when given a large slot; this is easily obtained in the present embodiment.

The diaphragm is motor-adjustable and the operating mechanism includes two operating members which are adjustably seated, similar to the diaphragm plates, and which are electrically coupled to the diaphragm plates via a feedback control unit. In this embodiment of the invention the operating mechanism allows for simple adjustment of the diaphragm. The technician actuates the operating mechanism in the direction the diaphragm is to be adjusted.

DESCRIPTION OF THE PREFERRED EMBODIMENTS

Figure 1:
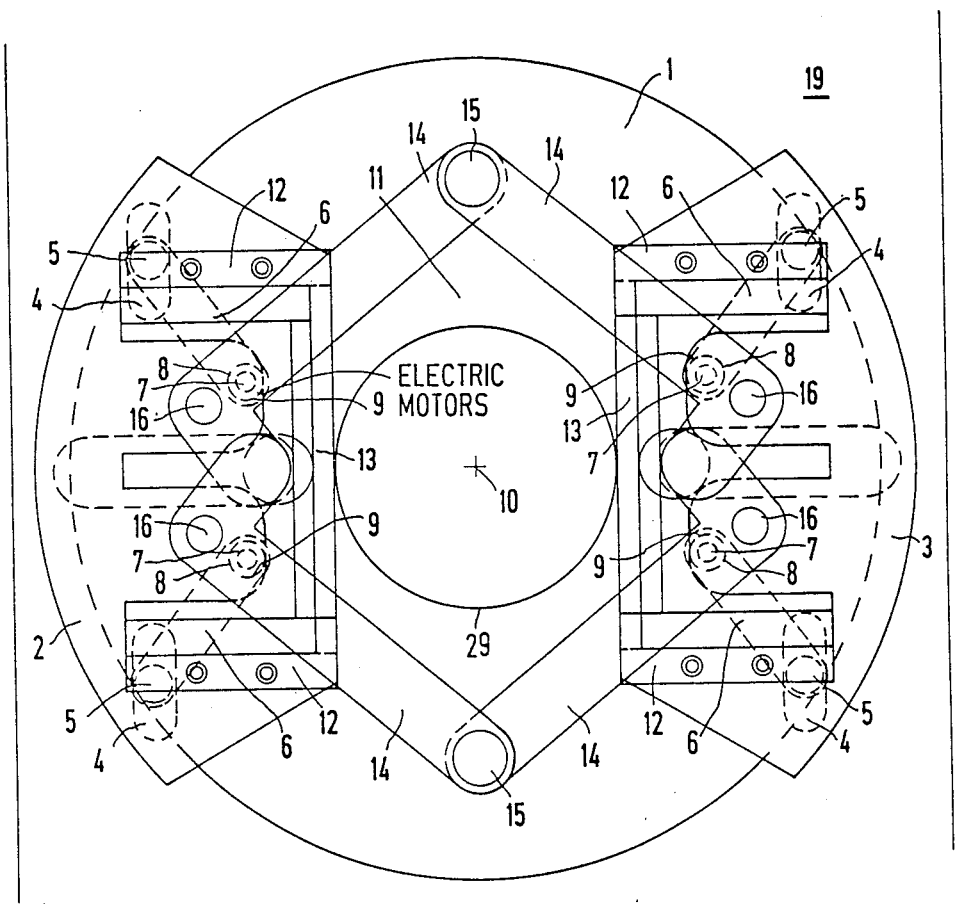
FIG. 1 is a plan view of a primary radiation diaphragm of the present invention.
Figure 2:
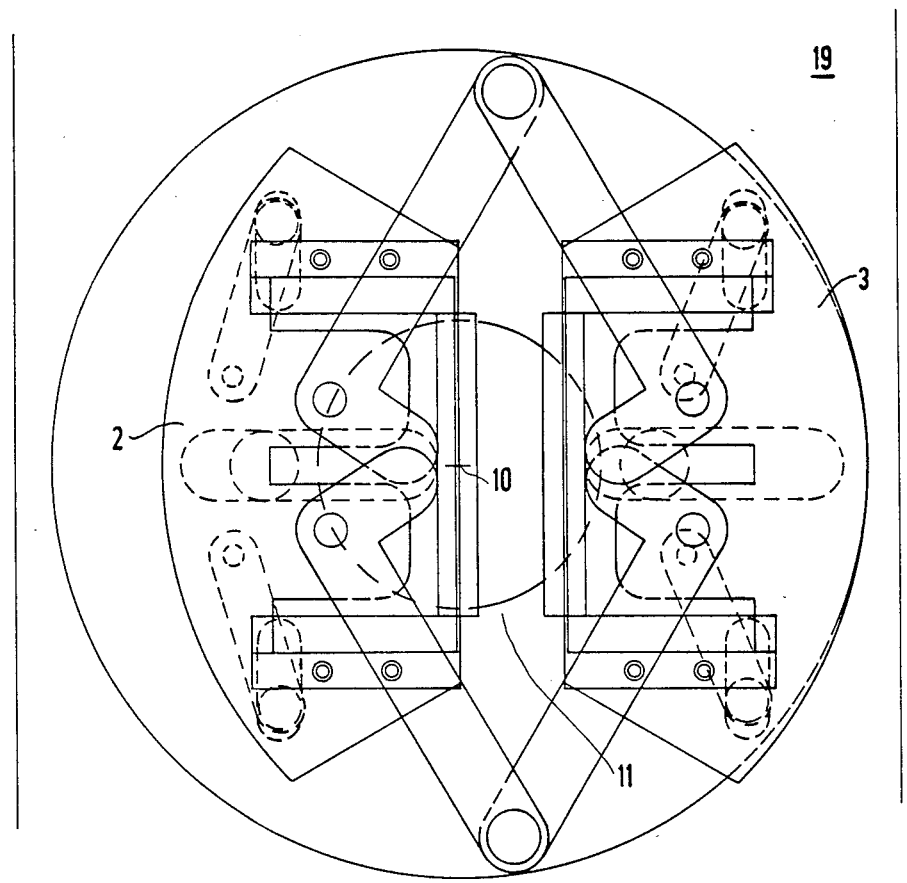
FIG. 2 is a plan view of a primary radiation diaphragm of the present invention wherein the slot lies asymmetric to the central ray.
Figure 3:
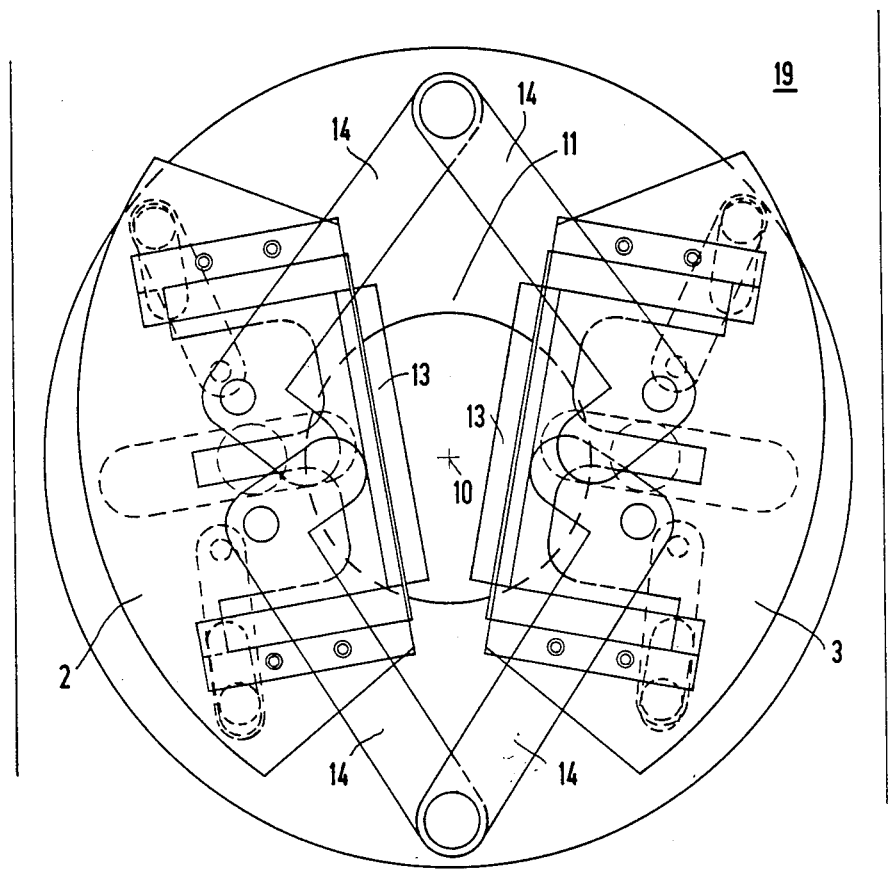
FIG. 3 is a plan view of a primary radiation diaphragm of the present invention wherein the slot is V-shaped.

As shown in FIGS. 1 through 3, the primary radiation diaphragm has a rotatable ring 1 on which two diaphragm plates 2 and 3 are adjustably seated for movement toward one another and away from one another. For this purpose, the diaphragm plates 2 and 3 have oblong holes 4 in which pins 5 are displaceably seated. The pins 5 are secured to levers 6. The levers 6 are respectively attached to shafts 7 which are driven with electric motors 8. The levers 6 are pivoted with the electric motors 8, thereby allowing for adjustment of the diaphragm plates 2 and 3. Since every lever 6 is individually pivotable, the diaphragm plates 2 and 3 are adjustable radially relative to the central ray 10 and obliquely relative thereto. Further, as a consequence of the four electric motors 8 the diaphragm plates 2 and 3 can be individually adjusted.

FIG. 2 shows the diaphragm plates 2 and 3 wherein the slot 11, limited by the diaphragm plates 2 and 3, lies asymmetrically relative to the central ray 10.

FIG. 3 shows the diaphragm plates 2 and 3 wherein the diaphragm plates 2 and 3 are adjusted to limit a V-shaped slot 11.

A further adjustment possibility for the slot 11 is established by turning the ring 1 together with the diaphragm plates 2 and 3.

As shown in FIGS. 1 through 3, the slot 11 limited by the diaphragm plates 2 and 3 can lie arbitrarily relative to the central ray 10, or asymmetrically relative thereto, and can be rectangularly shaped or V-shaped. This arbitary location of the slot 11 to the central ray 10 is achieved because the diaphragm plates 2 and 3 are individually adjustable in a two-dimensional fashion.

Proceeding from FIGS. 1 through 3, the diaphragm plates 2 and 3 have guides 12 in which semi-transparent diaphragm sections 13 are adjustably seated perpendicularly relative to the edges of the diaphragm plates 2 and 3 limiting the radiation. Angle levers 14 for the adjustment of the diaphragm sections 13 are included. These angle levers 14 are hinged to the ring 1 with articulations 15 and hinged to the diaphragm plates 2 and 3 with articulation 16. The angle levers 14 have their free ends lying against the inside of the semi-transparent diaphragm sections 13 which are pressed against these free ends of the angle levers 14 by spring means (not shown). For example, from FIG. 2, when the diaphragm plates 2 and 3 are closed, the free ends of the angle levers 14 press the diaphragm sections 13 in an inward direction, so that the semi-transparent region is set dependent on the diaphragm aperture such that it becomes larger as the diaphragm is closed.

As also shown by FIGS. 1 through 3, potentiometers 9 are respectively allocated to the shafts 7. These potentiometers 9 supply electrical signals that correspond to the positions of the levers 6 and, thus, to the positions of the diaphragm plates 2 and 3. These electrical signals are processed in a feedback control unit 16 shown in FIG. 4 so that the diaphragm has the position prescribed by an operating mechanism.

Figure 4:
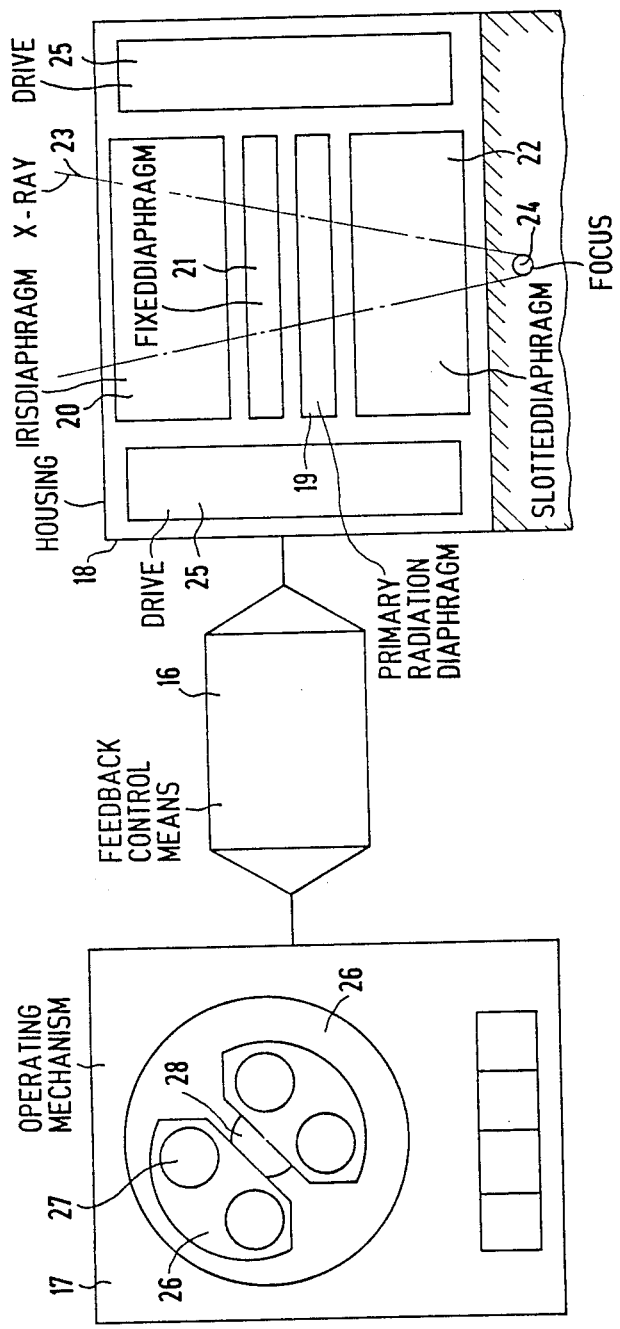
FIG. 4 is a schematic diagram of a primary radiation diaphragm of the present invention in combination with the allocated x-ray diagnostics equipment in an operating mechanism.

FIG. 4 schematically shows the housing 18 of the primary radiation diaphragm in x-ray examination equipment where an iris diaphragm 20, a fixed diaphragm 21 for a prescribed film format, and a slotted diaphragm 22 for gating rectangular diaphragm apertures are present in addition to the primary radiation diaphragm 19 that is constructed in accord with FIGS. 1 through 3. FIG. 4 shows the x-ray beam 23 that emanates from the focus 24 of an x-ray tube. The drives 25 and the allocated electronics are also schematically shown in the housing 18.

Following from FIG. 4, the operating mechanism 17 includes two operating plates 26 that are adjustable in the same way as the diaphragm plates 2 and 3, being adjustable with the assistance of a lever linkage that correponds to the lever linkage of FIGS. 1 through 3. The operating plates 26 have recesses 27 for the fingers of the operator. These plates 26 are easily adjustable therewith. A circle 28 that corresponds to the circle 29 in FIGS. 1 through 3 indicates the maximum diaphragm aperture. Analogous to the potentiometer 9 in FIGS. 1 through 3, potentiometers that supply rated value signals for the diaphragm aperture are allocated to the levers for the guidance of the operating plates 26. These rated value signals are compared in the feedback control unit 16 to the actual value signals supplied by the potentiometers 9 and the motors are driven in such a fashion that the actual value of the diaphragm aperture is matched to the rated value that has been set.

As is apparent from the foregoing specification, the invention is susceptible of being embodied with various alterations and modifications which may differ particularly from those that have been described in the preceding specification and description. It should be understood that we wish to embody within the scope of the patent warranted hereon all such modifications as reasonably and properly come with the scope of my contribution to the art.

I claim:

1. A primary radiation diaphragm for an x-ray diagnostics installation comprising:
    two diaphragm plates disposed in a plane and defining a diaphragm aperture therebetween through which x-radiation is admitted;
    means for adjustably seating said two diaphragm plates for permitting movement of said two diaphragm plates in said plane; and
    means for adjusting the positions of said two diaphragm plates in said plane in two dimensions so that said diaphragm aperture can be continuously changed in shape between a rectangular shape and a V-shape.

2. A primary radiation diaphragm as claimed in claim 1, further comprising:
    semi-transparent diaphragm sections at the edges of said diaphragm plates for limiting the x-radiation;
    means for adjustably attaching said semi-transparent diaphragm sections perpendicularly to said edges of the diaphragm plates so the semi-transparent region is adjusted dependent on the diaphragm aperture.

3. A primary radiation diaphragm as claimed in claim 2, further comprising:
    means for adjusting said semi-transparent region so that said semi-transparent region becomes larger when said diaphragm is closed.

4. A primary radiation diaphragm as claimed in claim 1, wherein said means for adjusting the positions of said diaphragm plates in two dimensions comprises:
    motors connected to said diaphragm plates for adjusting the positions of said diaphragm plates;
    two operating plates manually accessible by a user;
    means for adjustably positioning said two operating plates relative to each other;
    means for electrically coupling said two operating plates to said motors for positioning said diaphragm plates corresponding to the positions of said operating plates.

* * * * *